United States Patent
Gagne et al.

(10) Patent No.: US 10,502,650 B2
(45) Date of Patent: Dec. 10, 2019

(54) FLUID MONITORING DEVICE WITH DISPOSABLE INNER LINER WITH SENSOR INTEGRATION

(71) Applicant: ALPHINITY, LLC, Carson City, NV (US)

(72) Inventors: Michael C. Gagne, Carson City, NV (US); Steven V. Cates, Corona, CA (US); Dean C. Richards, Simi Valley, CA (US)

(73) Assignee: ALPHINITY, LLC, Carson City, NV (US)

( * ) Notice: Subject to any disclaimer, the term of this patent is extended or adjusted under 35 U.S.C. 154(b) by 0 days.

(21) Appl. No.: 16/275,189

(22) Filed: Feb. 13, 2019

(65) Prior Publication Data
US 2019/0178742 A1    Jun. 13, 2019

Related U.S. Application Data

(63) Continuation of application No. 15/656,762, filed on Jul. 21, 2017, which is a continuation of application (Continued)

(51) Int. Cl.
*G01D 11/24* (2006.01)
*G01L 19/14* (2006.01)
(Continued)

(52) U.S. Cl.
CPC ........... *G01L 19/14* (2013.01); *G01L 9/0026* (2013.01); *G01L 19/0023* (2013.01); *G01L 19/0038* (2013.01); *G01N 27/10* (2013.01)

(58) Field of Classification Search
CPC .......... G01D 11/24; G01D 11/245; G01F 1/66
(Continued)

(56) References Cited

U.S. PATENT DOCUMENTS 2,337,264 A * 12/1943 Nissen, Jr. ............. B65D 35/12
                                                              222/107
2,931,387 A    4/1960 Fleming
(Continued)

FOREIGN PATENT DOCUMENTS

EP          0522567 B1    10/1996
GB          1055426       1/1967
(Continued)

OTHER PUBLICATIONS

BioWorks LLC Product Brochure (date: unknown), BSC: Bio Sample Cup, Safe, Sanitary Material Storage, Easton, PA 18042, www.BioWorksLLC.com (undated) (6 pages).
(Continued)

*Primary Examiner* — Jamel E Williams
(74) *Attorney, Agent, or Firm* — Vista IP Law Group LLP

(57) ABSTRACT

A fluid monitoring assembly includes a segment of tubing having a wall defining a lumen through which the fluid passes and a sensor at least partially embedded within a wall of the tubing. The assembly includes a housing having first and second portions connected to one another at a hinge, the housing defining an interior portion configured to hold the segment of tubing and the sensor. The housing may be opened and closed as needed using a fastener.

14 Claims, 13 Drawing Sheets

Related U.S. Application Data

No. 15/032,257, filed as application No. PCT/US2014/062986 on Oct. 29, 2014, now Pat. No. 9,746,391.

(60) Provisional application No. 61/897,531, filed on Oct. 30, 2013.

(51) Int. Cl.
*G01N 27/10* (2006.01)
*G01L 19/00* (2006.01)
*G01L 9/00* (2006.01)

(58) Field of Classification Search
USPC .................................................. 73/861.25
See application file for complete search history.

(56) References Cited

U.S. PATENT DOCUMENTS

| | | | |
|---|---|---|---|
| 3,245,432 A | 4/1966 | Pusch | |
| 3,563,095 A | 2/1971 | Robinson, Jr. | |
| 4,194,401 A | 3/1980 | Claassen et al. | |
| 4,254,797 A | 3/1981 | Mayeaux | |
| 4,840,068 A | 6/1989 | Mayhew, Jr. | |
| 4,884,452 A * | 12/1989 | Kaiser | G01L 19/0023 73/730 |
| 4,895,341 A | 1/1990 | Brown | |
| 5,197,708 A | 3/1993 | Campau | |
| 5,233,868 A * | 8/1993 | Coats | G01F 1/6847 73/204.18 |
| 5,350,290 A | 9/1994 | Honings | |
| 5,410,916 A | 5/1995 | Cook | |
| 5,505,092 A * | 4/1996 | Kowalski | G01L 9/0002 338/4 |
| 5,549,134 A | 8/1996 | Browne et al. | |
| 5,639,972 A * | 6/1997 | Hastings | G01F 1/662 374/117 |
| 5,713,388 A | 2/1998 | Brewer | |
| 5,721,383 A * | 2/1998 | Franklin | G01F 1/075 73/861.77 |
| 5,817,926 A * | 10/1998 | Brandes | F16L 9/18 73/40.5 R |
| 6,012,339 A | 1/2000 | Genack et al. | |
| 6,036,166 A | 3/2000 | Olson | |
| 6,068,751 A | 5/2000 | Neukermans | |
| 6,164,143 A * | 12/2000 | Evans | G01F 1/46 73/52 |
| 6,196,519 B1 | 3/2001 | Utterberg | |
| 6,280,408 B1 | 8/2001 | Sipin | |
| 6,543,483 B2 | 4/2003 | Johnson | |
| 6,554,589 B2 | 4/2003 | Grapes | |
| 6,631,736 B2 | 10/2003 | Seitz et al. | |
| 6,644,353 B1 | 11/2003 | Eidsmore | |
| 6,957,588 B1 * | 10/2005 | Kicher | G01L 9/0027 73/720 |
| 6,976,664 B2 | 12/2005 | Welch et al. | |
| 6,981,410 B2 * | 1/2006 | Seki | G01F 1/6845 73/204.26 |
| 7,025,580 B2 * | 4/2006 | Heagy | B29C 63/34 138/108 |
| 7,058,549 B2 * | 6/2006 | Gysling | G01F 1/7082 702/189 |
| 7,104,275 B2 | 9/2006 | Dille | |
| 7,159,472 B1 | 1/2007 | Hastings | |
| 7,367,363 B2 | 5/2008 | Friedline et al. | |
| 7,383,853 B2 | 6/2008 | Welch et al. | |
| 7,624,632 B1 * | 12/2009 | Hoyle | G01M 3/2807 73/204.11 |
| 7,788,047 B2 | 8/2010 | Schick et al. | |
| 7,857,506 B2 | 12/2010 | Schick et al. | |
| 7,861,608 B2 | 1/2011 | Furey et al. | |
| 7,927,010 B2 | 4/2011 | Schick et al. | |
| 8,212,655 B2 * | 7/2012 | Nelson | G01D 21/00 340/10.41 |
| 8,302,496 B2 | 11/2012 | Furey et al. | |
| D671,853 S | 12/2012 | Furey et al. | |
| D684,076 S | 6/2013 | Furey et al. | |
| 8,489,342 B2 | 7/2013 | Dugger | |
| 8,506,162 B2 | 8/2013 | Schick et al. | |
| 8,770,010 B1 * | 7/2014 | Shapiro | A61M 39/08 73/37 |
| 8,919,365 B2 | 12/2014 | Hillier et al. | |
| 8,985,154 B2 * | 3/2015 | Quigley | F16L 11/12 138/33 |
| 9,181,941 B2 | 11/2015 | Cirou et al. | |
| 9,188,468 B2 * | 11/2015 | Rath | G01F 15/14 |
| 2004/0163711 A1 | 8/2004 | Varone | |
| 2004/0232923 A1 | 11/2004 | Farruggia et al. | |
| 2006/0010989 A1 | 1/2006 | Clark et al. | |
| 2006/0144155 A1 | 7/2006 | Liu | |
| 2007/0058690 A1 | 3/2007 | Feldmeier | |
| 2007/0139039 A1 | 6/2007 | Steinich | |
| 2007/0255527 A1 | 11/2007 | Schick et al. | |
| 2007/0278155 A1 | 12/2007 | Lo et al. | |
| 2007/0295867 A1 | 12/2007 | Hennon | |
| 2008/0035227 A1 | 2/2008 | Woods et al. | |
| 2008/0237509 A1 | 10/2008 | Yamamoto | |
| 2008/0277015 A1 | 11/2008 | Tanaka et al. | |
| 2009/0120503 A1 * | 5/2009 | Donahue | F16K 15/031 137/1 |
| 2009/0180513 A1 | 7/2009 | Schick et al. | |
| 2009/0241677 A1 | 10/2009 | Klees et al. | |
| 2011/0219885 A1 * | 9/2011 | Shumilov | G01F 1/3209 73/861.24 |
| 2012/0018654 A1 | 1/2012 | Wennberg et al. | |
| 2012/0242993 A1 | 9/2012 | Schick et al. | |
| 2013/0036844 A1 | 2/2013 | Furey et al. | |
| 2013/0080081 A1 * | 3/2013 | Dugger | G01F 1/667 702/48 |
| 2013/0171265 A1 | 7/2013 | Saxena et al. | |
| 2013/0213130 A1 | 8/2013 | Ohmiya et al. | |
| 2013/0213140 A1 | 8/2013 | Eichhorn et al. | |
| 2013/0305839 A1 | 11/2013 | Muench et al. | |
| 2014/0224335 A1 | 8/2014 | Hofmann | |
| 2014/0311254 A1 * | 10/2014 | Evans | G01F 1/40 73/861.61 |
| 2015/0013467 A1 | 1/2015 | Imai et al. | |
| 2015/0323486 A1 | 11/2015 | Schick et al. | |
| 2016/0327416 A1 * | 11/2016 | Gagne | G01F 15/14 |

FOREIGN PATENT DOCUMENTS

| | | | |
|---|---|---|---|
| JP | 2004293769 A | | 10/2004 |
| KR | 20150068207 A | * | 6/2015 |
| KR | 20150068207 A | | 6/2015 |
| WO | 97/26542 A1 | | 7/1997 |
| WO | 2010/137392 A1 | | 12/2010 |
| WO | 2012/143693 A1 | | 10/2012 |
| WO | 2013/044195 A2 | | 3/2013 |
| WO | 2013/125317 A1 | | 8/2013 |

OTHER PUBLICATIONS

Parker Mitos Product Brochure, Mitos Free Flow Valve, Apr. 29, 2009, http://www.mitostech.com/freelow.html (2 pages).

PCT International Search Report for PCT/US10/34371, Applicant: AlphaBio, Inc., Form PCT/ISA/210 and 220, dated Jul. 1, 2010 (4 pages).

PCT Written Opinion of the International Search Authority for PCT/US10/34371, Applicant: AlphaBio, Inc., Form PCT/ISA/237, dated Jul. 1, 2010 (7 pages).

PCT International Preliminary Report on Patentability (Chapter I of the Patent Cooperation Treaty) for PCT/US2010/034371, Applicant: AlphaBio, Inc., Form PCT/IB/326 and 373, dated Nov. 15, 2011 (9 pages).

The extended European search report dated Nov. 29, 2016 in European Application No. 10775392.3-1751, Applicant: Alphinity, LLC, (10pages).

BioWorks LLC, http://bioworksllc.com/pdf/BTV_Manifold_Brochure_rev1.pdf, Pub. Date May 19, 2016 (Wayback Machine).

(56) References Cited

OTHER PUBLICATIONS

Supplementary Search Report dated May 15, 2017 in European Patent Application No. 14 85 7877, (10pages).
Supplementary Search Report dated Feb. 28, 2018 in European Patent Application No. 14 85 7877, (8pages).
Communication pursuant to Article 94(3) EPC dated Dec. 20, 2018 for European Patent Application No. 14857877.6, Applicant: Alphinity, LLC, (5pages).
PCT International Search Report for PCT/US2014/062986, Applicant: Alphabio, Inc., Form PCT/ISA/210 and 220, dated Feb. 19, 2015 (4pages).
PCT Written Opinion of the International Search Authority for PCT/US2014/062986, Applicant: Alphabio, Inc., Form PCT/ISA/237, dated Feb. 19, 2015 (7pages).
PCT International Preliminary Report on Patentability (Chapter I of the Patent Cooperation Treaty) for PCT/US2014/062986, Applicant: Alphinity, LLC, Form PCT/IB/326 and 373, dated May 12, 2016 (9pages).

* cited by examiner

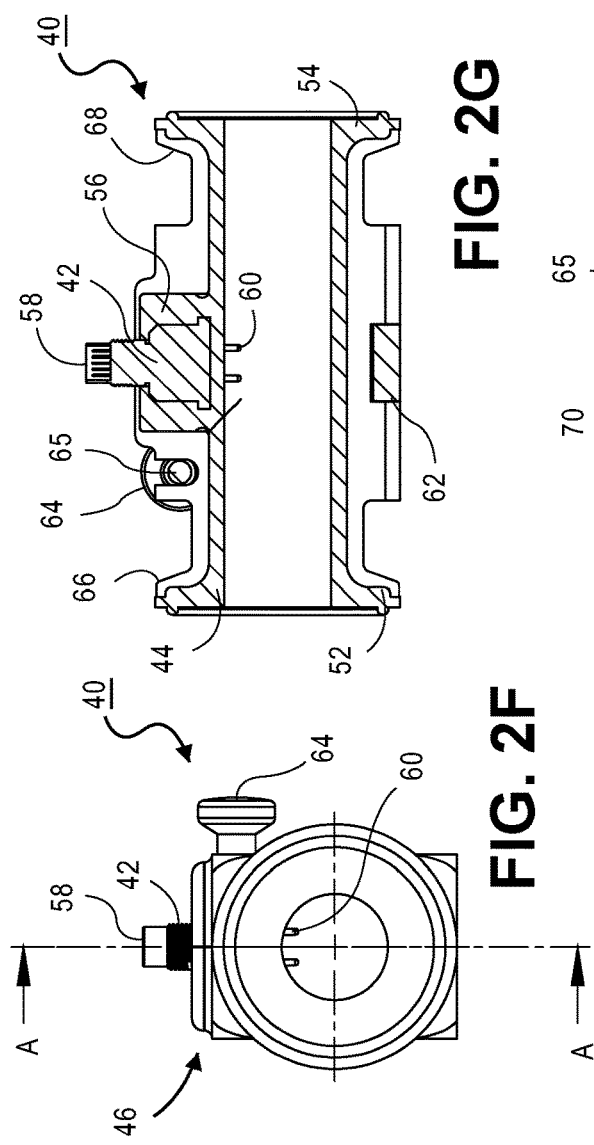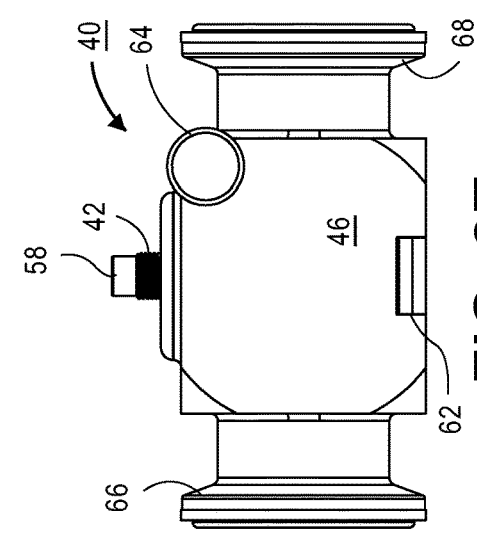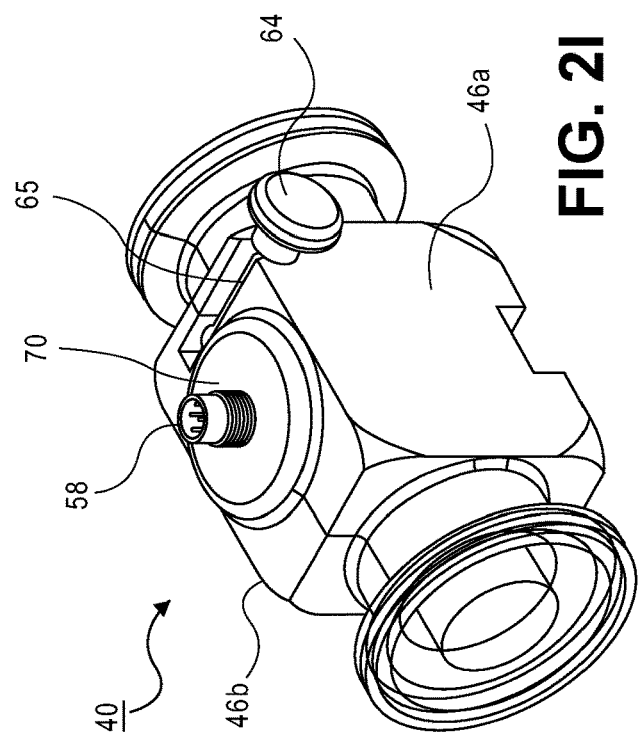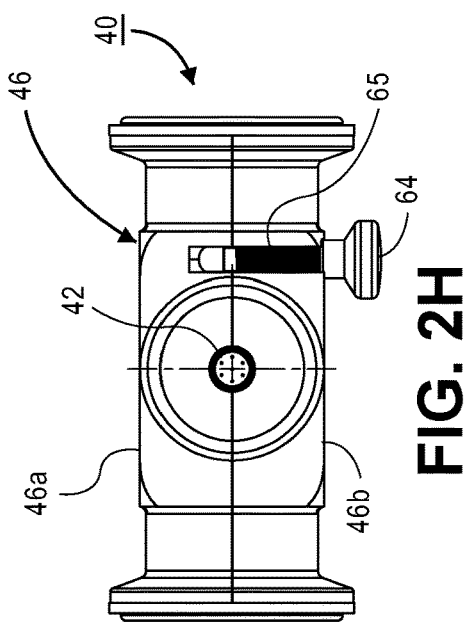

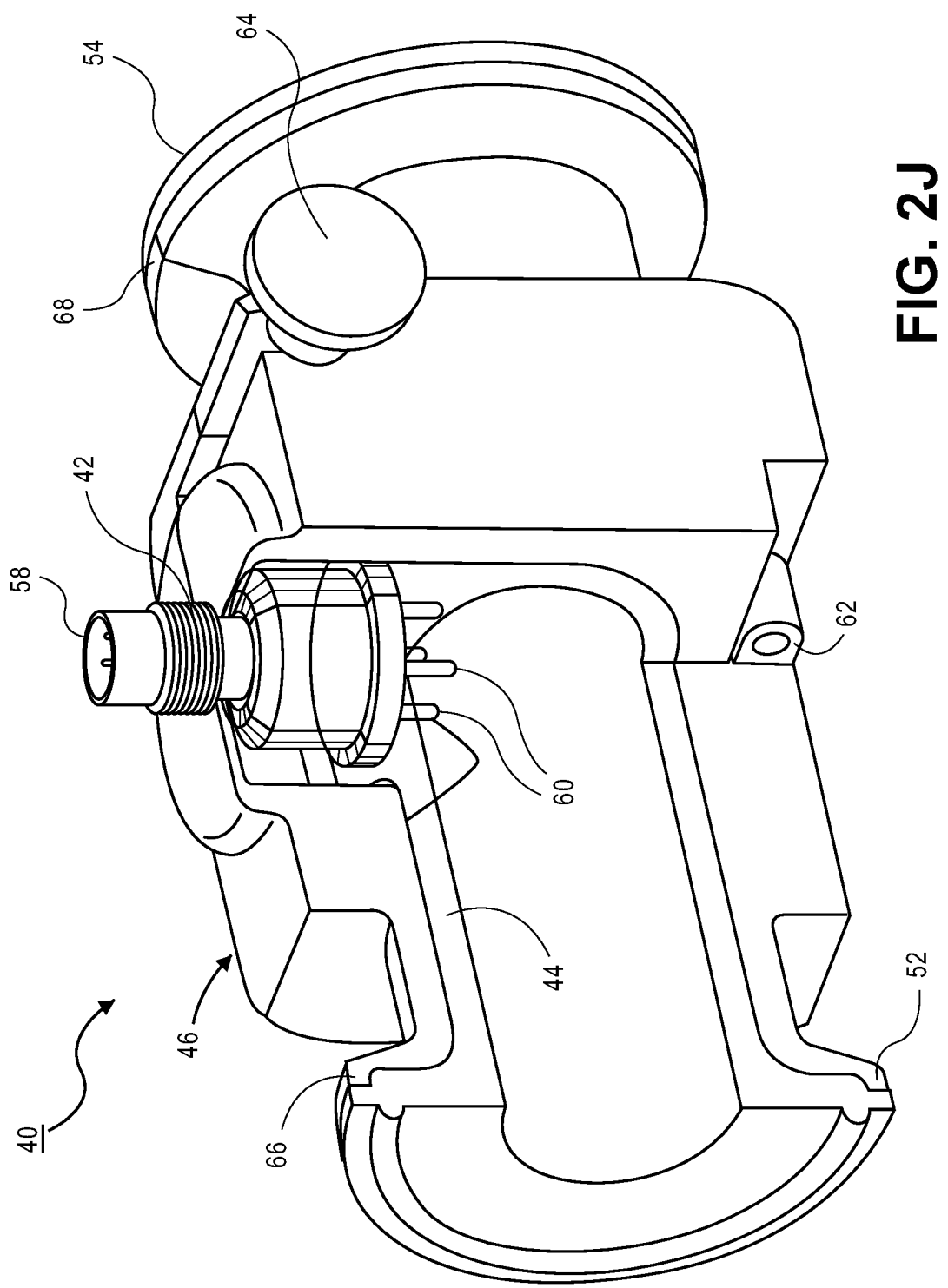

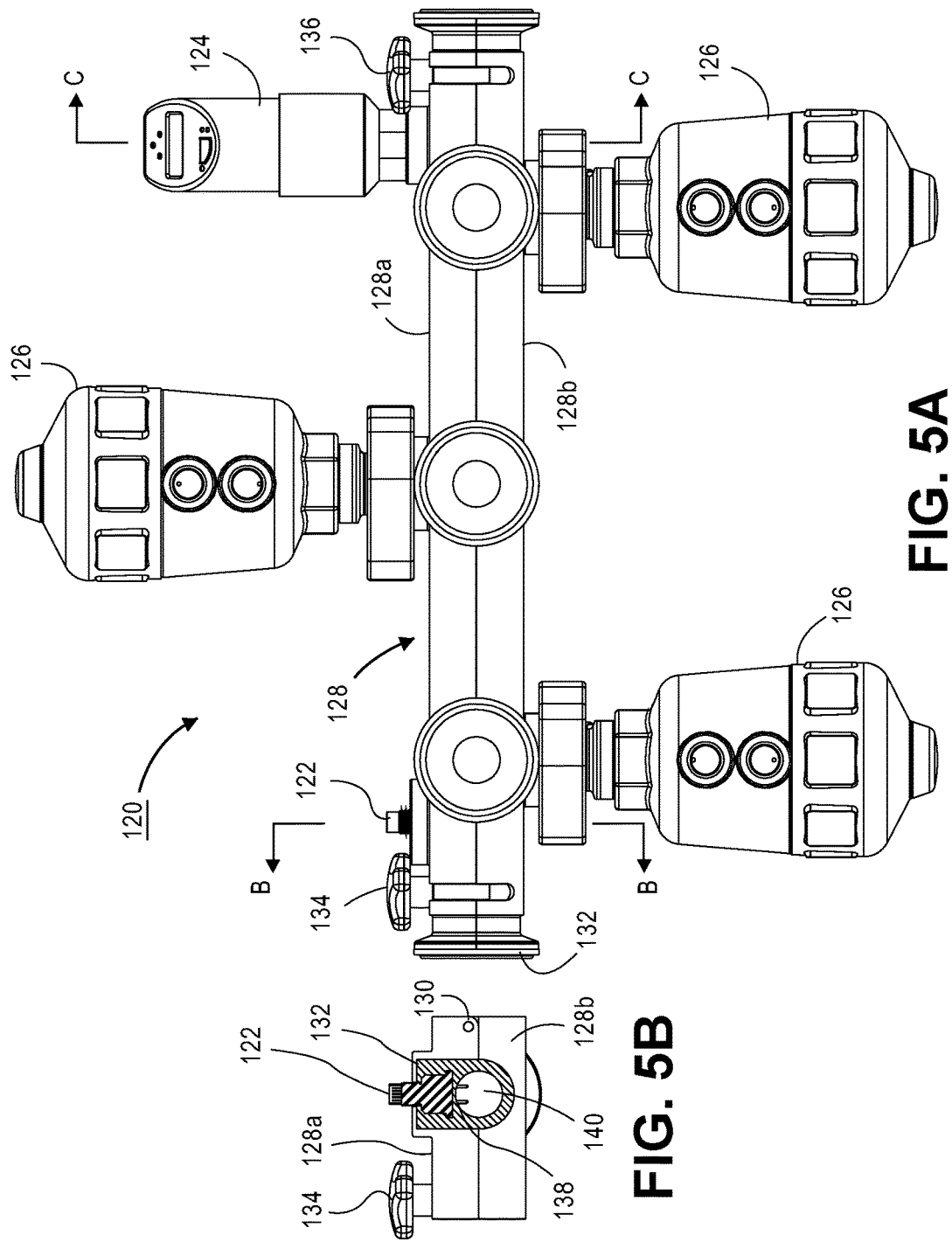

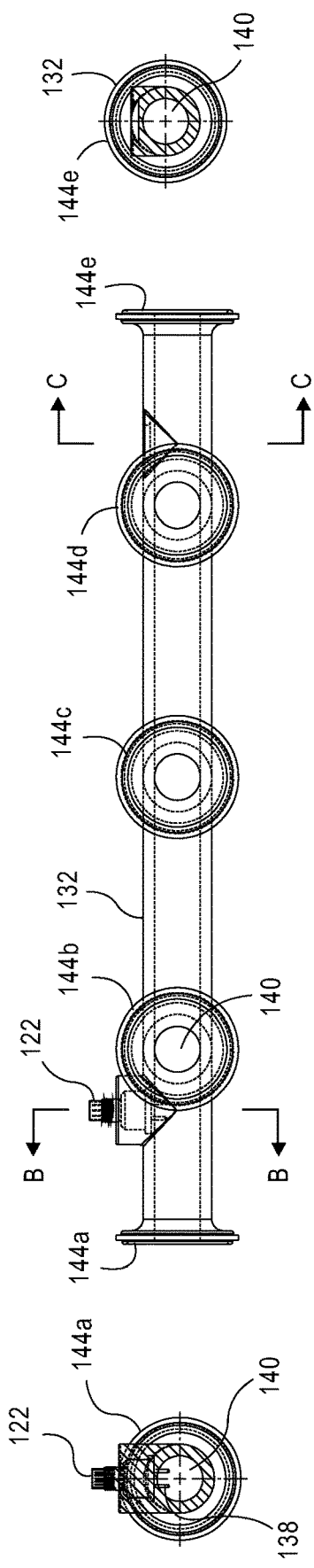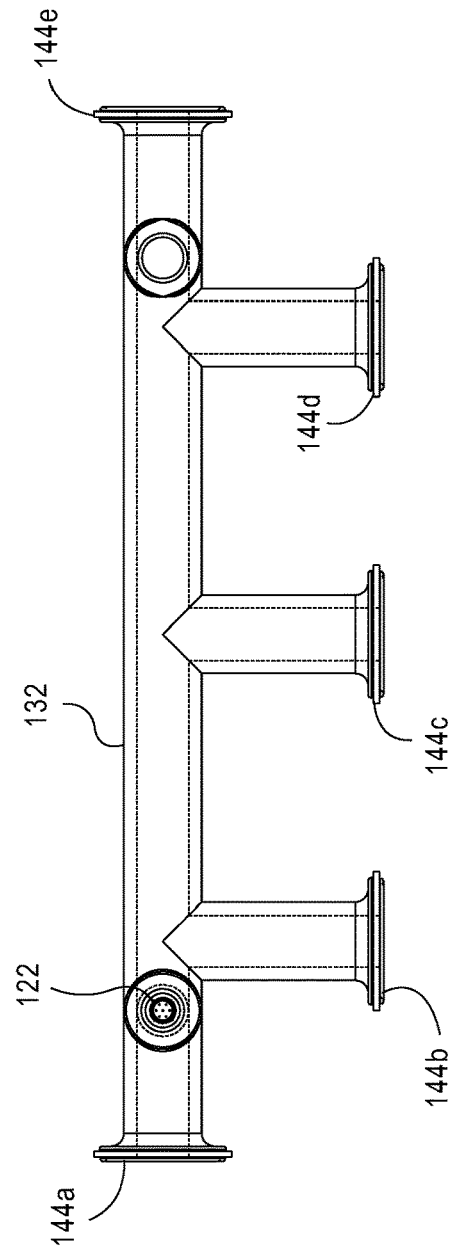

FLUID MONITORING DEVICE WITH DISPOSABLE INNER LINER WITH SENSOR INTEGRATION

RELATED APPLICATION

This Application is a continuation of U.S. application Ser. No. 15/656,762, now allowed, which is a continuation of U.S. application Ser. No. 15/032,257, now issued as U.S. Pat. No. 9,746,391, which itself is a U.S. National Stage filing under 35 U.S.C. § 371 of PCT Patent Application No. PCT/US2014/062986, filed Oct. 29, 2014, which claims priority to U.S. Provisional Patent Application No. 61/897,531 filed on Oct. 30, 2013. The contents of the aforementioned applications are incorporated by reference herein. Priority is expressly claimed in accordance with 35 U.S.C. §§ 119, 120, 365 and 371 and any other applicable statutes.

FIELD OF THE INVENTION

The field of the invention generally relates to fluid monitoring devices and, in particular segments of conduit or tubing that incorporate sensor functionality. More specifically, the invention pertains to connectors or interfaces used by pharmaceutical and biological applications or other hygienic process industries involving silicone tubing or other conduits that include sensors therein.

BACKGROUND

Many commercial products are produced using chemical as well as biological processes. Pharmaceuticals, for example, are produced in commercial quantities using scaled-up reactors and other equipment. So-called biologics are drugs or other compounds that are produced or isolated from living entities such as cells or tissue. Biologics can be composed of proteins, nucleic acids, or complex combinations of these substances. They may even include living entities such as cells. In order to produce biologics on a commercial scale, sophisticated and expensive equipment is needed. In both pharmaceutical and biologics, for example, various processes need to occur before the final product is obtained. For example, in the case of biologics, cells may be grown in a growth chamber or the like and nutrients may need to be carefully modulated into the growth chamber. Waste products produced by cells may also have to be removed on a controlled basis from the fermentation chamber. As another example, biologic products produced by living cells or other organisms may need to be extracted and concentrated. This process may involve a variety of filtration and separation techniques.

Because there are a number of individual processes required to be produce the final product, various reactants, solutions, and washes are often pumped or otherwise transported to various subsystems using conduits and associated valves. These systems may be quite cumbersome and organizationally complex due to the large numbers of conduits, valves, sensors, and the like that may be needed in such systems. Not only are these systems visually complex (e.g., resembling spaghetti) they also include many components that are required to be sterilized between uses to avoid cross-contamination issues. Indeed, the case of drug and biologic preparation, the Federal Food and Drug Administration (FDA) is becoming increasingly strict on cleaning, sterilization or bio-burden reduction procedures that are required for drug and pharmaceutical preparations. This is particularly of a concern because many of these products are produced in batches which would require repeated cleaning, sterilization or bio-burden reduction activities on a variety of components.

During the manufacturing process of pharmaceuticals and biologics there often is a need to incorporate sensors into the manufacturing process so that process variables are monitored. For example, the process variables that need to be monitored may include temperature, pressure, pH, conductivity, and the like. In conventional setups, sensors are placed directly along one or more points of the production process whereby the sensors themselves are inserted into the production stream where the sensor makes direct contact with the reactant or product stream. Direct contact of the sensor with the reactant or the product stream may result in potential contamination issues. Further, in conventional manufacturing processes, the sensors may need to be changed, for example, due to a malfunction or because the product being manufactured requires a different sensor. In these examples, it can be a time consuming and expensive process to replace these sensors and also ensuring that reactants or products remain uncontaminated.

SciLog BioProcessing Systems, for example, produces a line of single use disposable sensors for use with bioprocessing application. These include pressure sensors, temperature sensors, and conductivity sensors. In the SciLog sensors, however, portions of the sensing elements come into contact with the fluid passing through the unit. Moreover, the entire unit is thrown away including the tubing, sensor, and associated housing. U.S. Pat. No. 7,788,047 discloses a disposable, pre-calibrated, pre-validated sensor for use in bioprocessing applications. In the '047 patent electrodes pins (204) are in contact with fluid passing along the interior of the conduit (102). The entire assembly containing the conduit and sensor is designed to be thrown away.

SUMMARY

According to one embodiment of the invention, a fluid monitoring assembly includes a segment of tubing having a wall defining a lumen through which the fluid passes. The assembly further includes a sensor at least partially embedded within a wall of the tubing. The assembly includes a housing having first and second portions connected to one another at a hinge, the housing defining an interior portion configured to hold the segment of tubing and the sensor. In one embodiment, the tubing is silicone. For example, the tubing may include UV-cured silicone or in other embodiments, thermally cured silicone. The sensors may include a pressure sensor or a conductivity sensor. The housing may be opened and closed via a fastener.

According to another embodiment, a fluid pressure assembly includes a segment of tubing having a wall defining a lumen through which the fluid passes. The assembly includes a housing having first and second portions connected to one another at a hinge, the housing defining an interior portion configured to hold the segment of tubing. The assembly includes a pressure sensor having a pressure sensing end in contact with a portion of the wall, wherein fluid pressure within the lumen is transmitted through the wall to the pressure sensing end. In one embodiment, the tubing may be made from silicone. The silicone may be thermally cured or UV-cured.

According to another embodiment, a method of changing a fluid monitoring assembly that includes a segment of tubing having a wall defining a lumen through which the fluid passes, a sensor embedded within a wall of the tubing, and a housing having first and second portions connected to one another at a hinge, the housing defining an interior portion configured to hold the segment of tubing and the sensor. The method includes opening the housing, removing the tubing, inserting a second tubing containing a sensor into the housing; and closing the housing. The sensor in the second tubing may be the same or different sensor.

In another embodiment, a method of forming a fluid monitoring assembly includes inserting a sensor into a cavity of a mold; injecting a liquid silicone rubber into the mold cavity, wherein the liquid silicone rubber at least partially surrounds a portion of the sensor; and applying UV radiation to the liquid silicone rubber to cure the silicone.

In another embodiment, a fluid monitoring assembly includes a segment of tubing having a wall defining a lumen through which the fluid passes. The assembly includes a housing having first and second portions connected to one another at a hinge, the housing defining an interior portion configured to hold the segment of tubing; and a conductivity sensor at least partially embedded in the wall of the segment of tubing, wherein the conductivity sensor further comprises a plurality of electrodes extending through the wall and into the lumen.

In another embodiment, a fluid assembly includes a segment of tubing having a wall defining a lumen through which the fluid passes; a housing having first and second portions defining an interior portion configured to hold the segment of tubing; at least one valve disposed on the housing and configured to pinch the segment of tubing; and one or more sensors at least partially embedded in the wall of the segment of tubing.

BRIEF DESCRIPTION OF THE DRAWINGS

FIG. 2E illustrates a side view of a fluid monitoring assembly according to one embodiment.

FIG. 2F illustrates an end view of the fluid monitoring assembly of FIG. 2E.

FIG. 2G illustrates a cross-sectional view of the fluid monitoring assembly of FIG. 2E taken along the line A-A.

FIG. 2H illustrates a top view of the fluid monitoring assembly of FIG. 2A.

FIG. 2I illustrates a perspective view of the fluid monitoring assembly of FIG. 2A.

FIG. 2J illustrates a partially cut-way view of the fluid monitoring assembly. A portion of one half of the housing is cut away to illustrate the silicone liner and other features.

FIG. 5A illustrates a side view of an alternative fluid management assembly that incorporates fluid monitoring.

FIG. 5B is a cross-sectional view taken along the line B-B of FIG. 5A.

FIG. 5C is a cross-sectional view taken along the line C-C of FIG. 5A.

FIG. 6A illustrates a liner used in the fluid management assembly of FIGS. 5A-5E FIG. 6B illustrates a cross-sectional view taken along the line B-B of FIG. 6A.

FIG. 6C illustrates a cross-sectional view taken along the line C-C of FIG. 6A.

FIG. 6D illustrates a plan view of the liner.

DETAILED DESCRIPTION OF THE ILLUSTRATED EMBODIMENTS

Figure 1C:
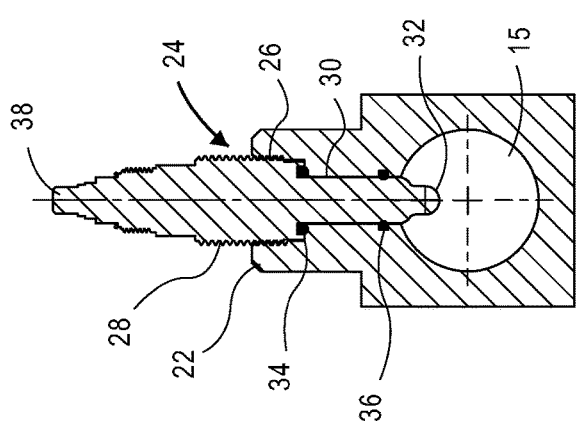
FIG. 1C illustrates a cross-sectional view of the fluid monitoring assembly taken along the line A-A of FIG. 1A.
Figure 1D:
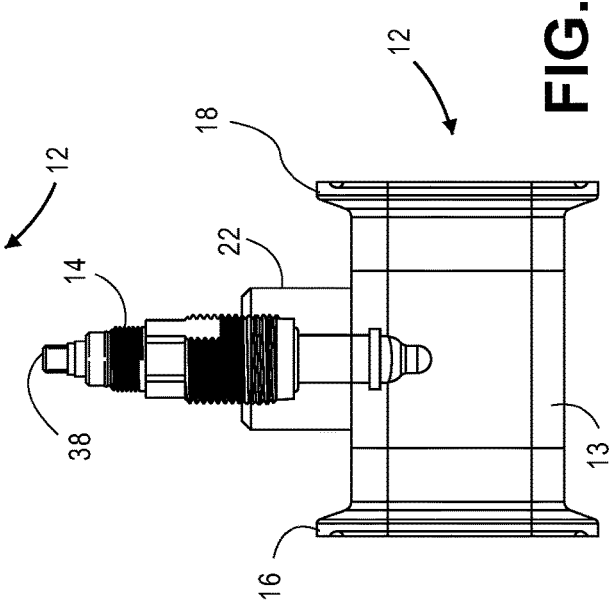
FIG. 1D illustrates a side view of the fluid monitoring assembly with the housing being partially transparent to illustrate the pH sensor contained therein.
Figure 1A:
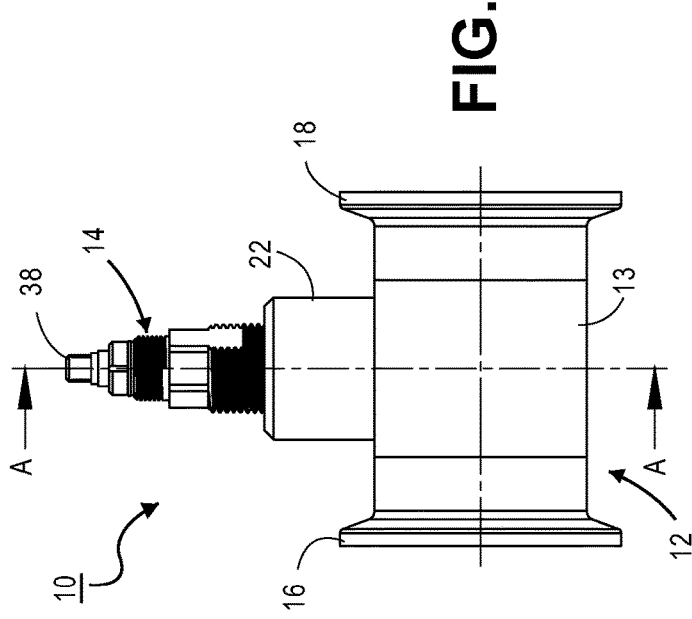
FIG. 1A illustrates a side view of a fluid monitoring assembly according to one embodiment.
Figure 1B:
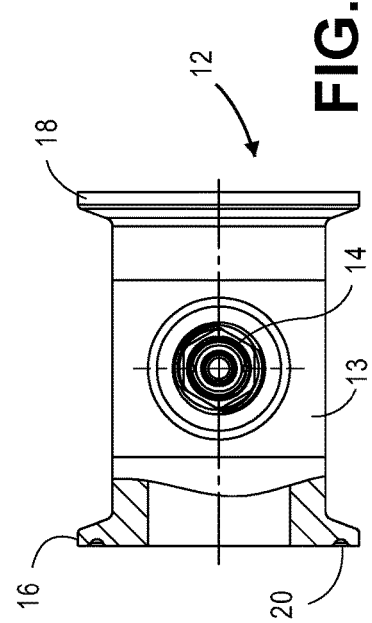
FIG. 1B illustrates a top down view of the fluid monitoring assembly of FIG. 1A.

FIGS. 1A-1D illustrate one embodiment of a fluid monitoring assembly 10 according to one embodiment. The fluid monitoring assembly 10 is designed as a single-use, disposable device. The fluid monitoring assembly 10 includes a housing 12 that contains a pH sensor 14. The housing 12 includes a conduit segment 13 having a lumen 15 (best seen in FIG. 1C) extending within the conduit segment 13 which fluid passes through. The conduit segment 13 terminates at opposing ends with flanges 16, 18. The housing 12 illustrated in FIG. 1C is unitary body in which the flanges 16, 18 are integrated on opposing ends of the conduit segment 13. The conduit segment 13 may be formed as a cylindrical tubing although other geometries are contemplated. Flanges 16, 18 are designed to mate with corresponding flanges (not shown) contained in fluid line of a manufacturing process. In this regard, the fluid monitoring assembly 10 may be inserted at desired locations so that the pH sensor 14 may be easily added or removed as necessary. Typically, the respective facing surfaces of the flanges 16, 18 (and opposing ends) are held together via a clamp or the like. An o-ring or other seal (not shown) may be provided in a groove 20 contained in the flanges 16, 18 for sealing purposes (as seen in FIG. 1B).

In other alternative embodiments, the flanges 16, 18 may be omitted and the housing 12 may extend laterally beyond the portion containing the sensor 14 without any mating surface or flange type structure.

The housing 12 further includes a mounting section 22 that is oriented generally perpendicular to the long axis of the conduit segment 13 and includes a bore 24 (FIG. 1C) that is configured to receive the pH sensor 14. In this embodiment, a portion of the bore 24 is threaded 26 such that corresponding threads 28 contained on the pH sensor 14 interface therewith. The pH sensor 14 includes a shank portion 30 that terminates in a sensing end 32. The sensing end 32 of the pH sensor 14 extends into the lumen 15 so as to expose the sensing end 32 passing fluid. A pair of o-rings 34, 36 are disposed about the shank portion 30 of the pH sensor 14 and serve to seal the pH sensor 14 relative to the housing 12.

In this embodiment, the pH sensor 14 has a reduced length which is typically less than around 3 inches for use with a housing 12 having lumen 15 internal diameter of 1.0 inches. Of course, other sized housings 12 may are contemplated (e.g., 3.4 inch I.D.). The pH sensor 14 can be screwed into the mounting section 22 of the housing 12. Optionally, one or more sealants, adhesives, glues may be used in addition to the o-rings 34, 36 to aid is sealing the pH sensor 14 within the housing 12. In one preferred embodiment, the housing 12 is typically made from a polymer material such as plastic materials. Materials include standard thermoplastics and polyolefins such as polyethylene (PE) and polypropylene (PP). The housing 12 may also be formed from fluoropolymers such as polyvinylidene fluoride (PVDF) or perfluoroalkoxy (PFA), polytetrafluoroethylene (PTFE), polycarbonate (which may be more thermally resistant), polysulfone (PSU), and the like. The housing 12 may also be made out of a metal. The pH sensor 14 includes an end or connector 38 located on an exposed portion of the pH sensor 14 which can be connected via wires (or in other embodiments wirelessly) to a pH reader (not shown).

Figure 2C:
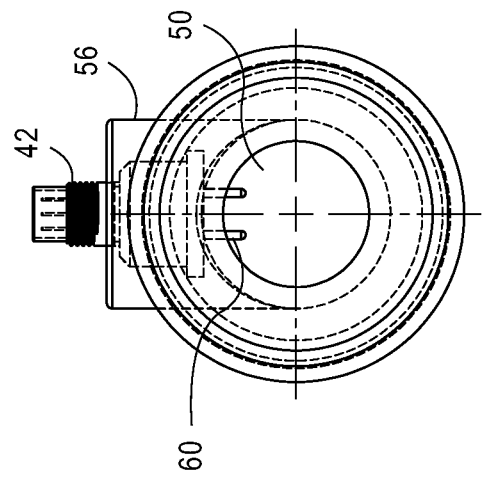
FIG. 2C illustrates an end view of the silicone liner of FIG. 2A.
Figure 2D:
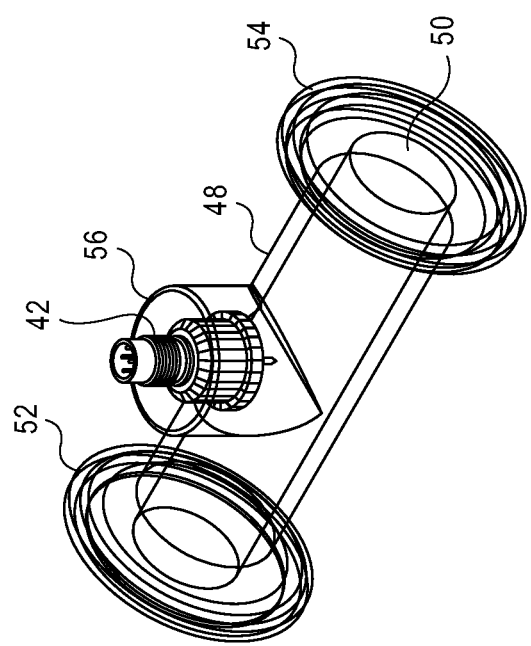
FIG. 2D illustrates a perspective view of the silicone liner of FIG. 2A.
Figure 2A:
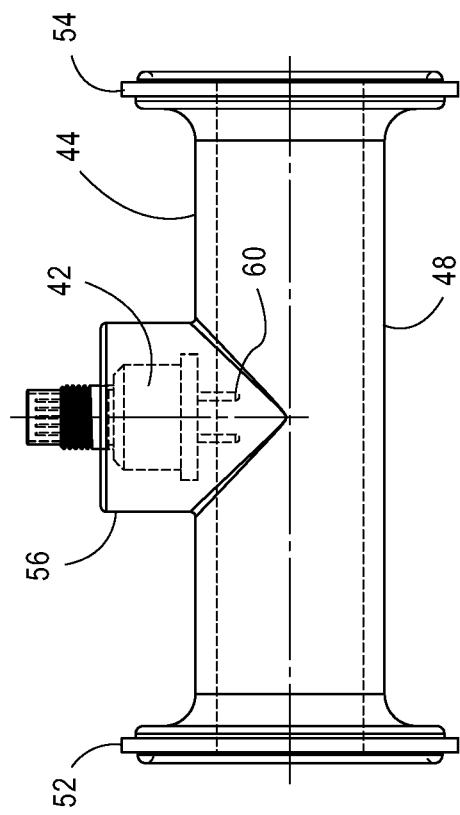
FIG. 2A illustrates a side view of a silicone liner (e.g., tubing) containing a conductivity sensor according to one embodiment.
Figure 2B:
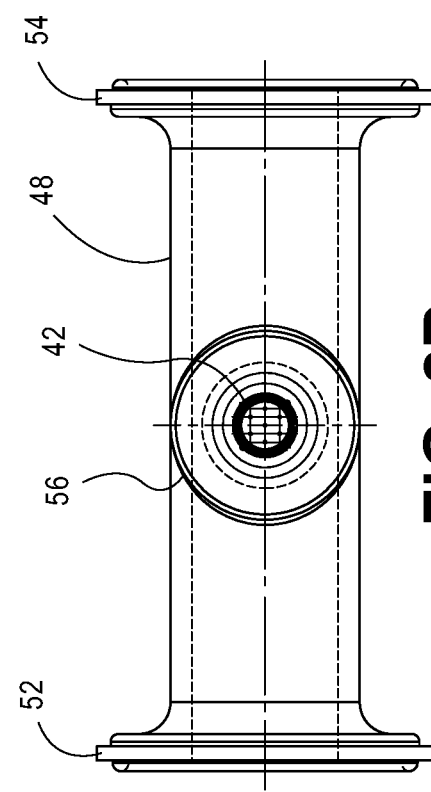
FIG. 2B illustrates a top view of the silicone liner of FIG. 2A.

FIGS. 2A-2J illustrate a fluid monitoring assembly 40 according to another embodiment. This embodiment pertains to a fluid monitoring assembly 40 that includes a conductivity sensor 42 that is embedded or potted within a liner 44 can then be loaded into a two-part housing 46 (seen in FIGS. 2E-2J). The liner 44 may, in one preferred embodiment, be made from silicone although other materials may be used. In this embodiment, the silicone liner 44 along with the embedded conductivity sensor 42 can be made disposable while the housing 46 can be re-used with another new or un-used silicone liner 44 with the conductivity sensor 42 contained therein. FIGS. 2A-2D illustrate a silicone liner 44 according to one embodiment. The silicone liner 44 includes a conduit segment 48 defining a wall and having a lumen 50 (best seen in FIG. 2C) extending within the conduit segment 48 which fluid passes through (e.g., a segment of silicone tubing). The conduit segment 48 terminates at opposing ends with silicone flanges 52, 54. The silicone flanges 52, 54 are dimensioned to reside within corresponding flanges (described below) in the two-part housing 46. The silicone liner 44 also includes a conductivity sensor 42 that is embedded or otherwise potted into a portion of the wall of the conduit segment 48. As best seen in FIGS. 2A and 2D, an overmolded portion 56 that extends outwardly from the wall of the conduit segment 48 contains the conductivity sensor 42. Substantially all or a portion of the conductivity sensor 42 is embedded within the silicone liner 44. A connector 58 is exposed outside of the overmolded portion 56 and is used to connect the conductivity sensor 42 via cabling, wiring, or the like. The conductivity sensor 42 may be a commercially available sensor or probe that is integrated into the silicone liner 44. Alternatively, the conductivity sensor 42 may include a variety of different kinds and makes of conductivity sensors. For example, the conductivity sensor 42 may include two, four, or a different number of electrodes. The electrodes may be made from various materials such as, for instance, gold or stainless steel.

As best seen in FIGS. 2A and 2C, the conductivity sensor 42 includes one or more electrodes 60 that project or extend inwardly from the wall of the conduit segment 48 so that the one or more electrodes 60 are exposed to the lumen 50 where the fluid resides. During the manufacturing process, portions (e.g., the base) of the one or more electrodes 60 are sealed against the molded silicone. This arrangement leaves portions of the electrodes 60 (e.g., tips or ends) that are exposed to the product passing through the lumen 50.

FIGS. 2I-2J illustrate the fluid monitoring assembly 40 after the silicone liner 44 that contains the conductivity sensor 42 has been inserted into the two-part housing 46. The two-part housing 46 includes a first half 46a and a second half 46b that are connected together via a hinge 62. The hinge 62 may be constructed, for example, as a rod or post that is contained within an aperture or bore that permits the first half 46a and second half 46b to pivot from a closed state to an open state so that the silicone liner 44 containing the conductivity sensor 42 can be easily removed and replaced. A fastener 64 such as a locking knob and associated locking arm 65 can be used to fixedly hold the two-part housing 46 in the closed state. Of course, other types of fasteners 64 can be used. These include screws, nuts, clamps, bands, ties, and the like. Multiple fasteners 64 may also be used. As best seen in FIG. 2G, the two-part housing 46 includes flanges 66, 68 that are sized to contain the corresponding silicone flanges 52, 54 of the silicone liner 44. In an alternative embodiment, the flanges 52, 54 of the liner 44 may be omitted along with the flanges 66, 68 of the housing 46. The housing 46 may thus extend laterally beyond the location of the conductivity sensor 42 and not terminate in a mating structure or flange-like surface. The housing 56 may continue on in any number of geometrical configurations. For example, the 56 housing may continue as a straight segment, a curved segment, elbow or the like.

FIG. 2G illustrates a cross-sectional view of the fluid monitoring assembly 40 taken along the line A-A of FIG. 2F. FIG. 2F shows how the silicone liner 44 remains nested within the two-part housing 46. The two-part housing 46 contains the conduit segment 48 as well as the overmolded portion 56 that contains the conductivity sensor 42. The two-part housing 46 provides an opening 70 (FIG. 2I) so that the connector 58 is exposed to the exterior environment and can be secured to appropriate cabling, wiring, or the like. In this embodiment, the two-part housing 46 is preferably made of a metal such as stainless steel. However, in alternative embodiments, the two-part housing 46 may be made from plastic or polymer materials. In this regard, the two-part housing 46 may be re-used while the silicone liner 44 and the conductivity sensor 42 may be disposable. Like the prior embodiment, the size of the fluid monitoring assembly 40 may vary. For example, without limiting the invention, the ID of the silicone liner 44 may be 1 inch although other sizes may also be used.

In order to create the silicone liner 44 with the embedded or potted conductivity sensor 42, a UV-curable Liquid Silicone Rubber (LSR) is used in one particular embodiment. For example, SILOPREN available from Momentive Performance Materials Inc. (Albany, N.Y.) is a UV cured LSR that may be used to form the silicone liner 44. SILOPREN is a two-component LSR what uses a mixing ratio of 100:2. Another example of a UV cured silicone is ADDISIL available from Momentive Performance Materials Inc. (Albany, N.Y.) which offers high cure speed at room temperatures. ADDISIL silicone rubber is a two component solution that uses a mixing ratio of 100:0.5 (Rubber Base:Catalyst). The benefits of using a UV curable LSR are numerous. First, there is no heating of the materials as is required in conventional silicone curing techniques. Thus, the silicone liner 44 may be formed at substantially room temperatures. If the silicone liner 44 described herein were to be formed with conventional thermally-cured silicone, embedded conductivity sensor 42 would melt, deform, or otherwise fail during the curing process. Here, using the UV curing process, the conductivity sensor 42 remains unaffected by the curing process. Because no heating is required, the process also has low energy consumption. Further, the UV curing process uses less equipment and can increase throughput as heating up and cool-down tend to consume a considerable amount of time. Another example of a UV curable silicone is the SEMICOSIL UV product made by Wacker Chemie AG (Munich, Germany).

Standard liquid silicone rubbers are processed in molds generally at temperatures between 180 and 200° C. UV-cured LSR parts can be made with transparent molds cured by UV light as explained herein. UV curing typically occurs at ambient or slightly above ambient temperatures (e.g., 25-40° C.). For thick parts, UV curing is advantageous because the product may cross-link much more quickly than with thermal curing because the low thermal conductivity of the silicone rubber is not a factor. Another advantage of UV curing is that the curing is initiated when the light is first turned on rather than on first contact with the heated mold. This difference eliminates the problem of silicone rubber scorching. Related to this, the liquid silicone (or other polymer) can be pumped into the mold relatively slowly and at low pressures.

Figure 3:
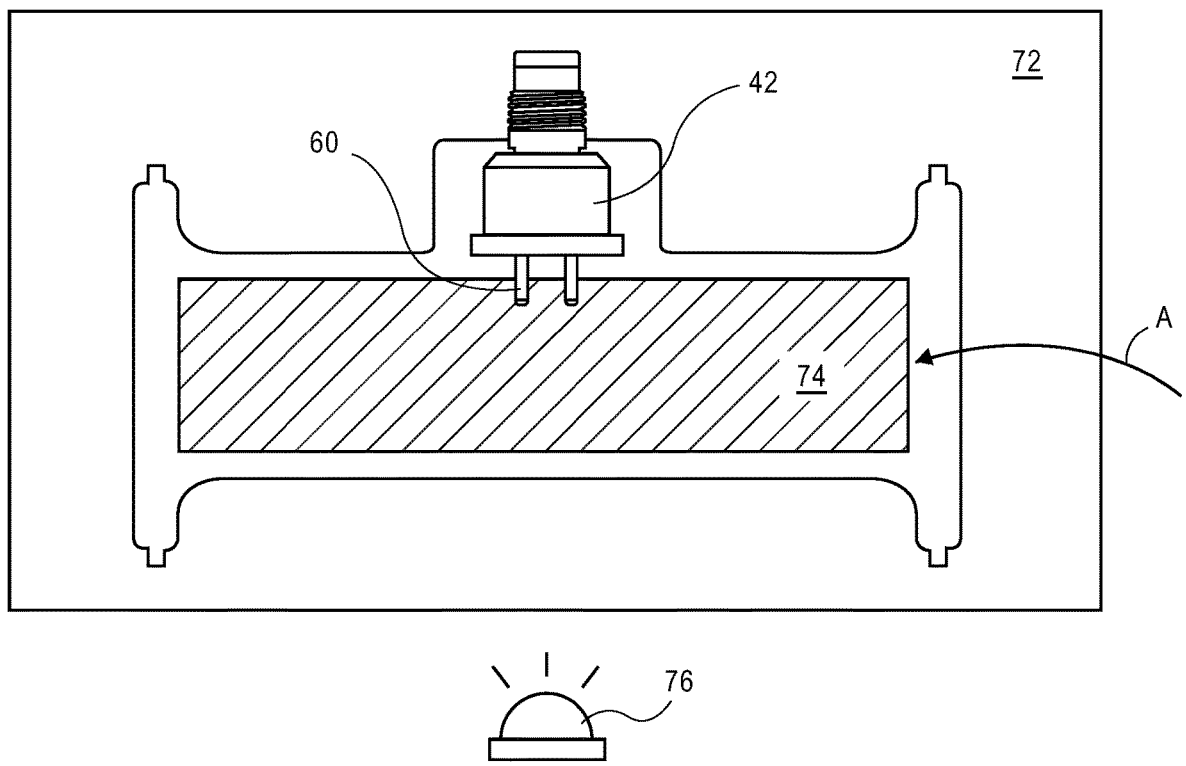
FIG. 3 illustrates a mold according to one embodiment used to manufacture the integrated silicone liner and sensor of the fluid monitoring assembly illustrated in FIGS. 2A-2J.

FIG. 3 illustrates a method of making the silicone liner 44 with the embedded conductivity sensor 42. In the method, a mold 72 is provided in which the conductivity sensor 42 is placed along with a core 74 that defines the lumen 50. Alternatively, the core 74 may be omitted and the portion defining the lumen 50 may be defined in the mold itself. The UV-curable LSR is then loaded into the mold 72 as indicated by arrow A. The UV-curable LSR is then subject to irradiation with UV light by source(s) 76 to cure the LSR into a solid form. After curing, the silicone liner 44 is embedded or potted within the wall of the silicone liner 44.

In other embodiments, it may be possible to mold the conductivity sensor 42 into a silicone liner 44 that is heat-cured rather than UV-cured. For example, the conductivity sensor 42 may be made from a high temperature plastic material (resistant to high temperatures) such that the thermal curing may be used to cure the silicone liner 44.

While FIGS. 2A-2J illustrate a fluid monitoring assembly 40 that includes a conductivity sensor 42, it should be understood that alternative sensors may be incorporated in this embodiment. For example, the sensor could be a pH sensor, a temperature sensor, a pressure sensor, turbidity sensor, or the like. In some alternative embodiments, the active region of the sensor may not need to come into direct contact with the fluid contained in with the silicone liner 44. For example, if the sensor is optical-based sensor it may be able to transmit a signal through a thin portion of the liner that can be detected on the opposing side. In such an example, there is no need for direct contact between the sensor and the fluid that passes through the silicone liner 44.

Figure 4A:
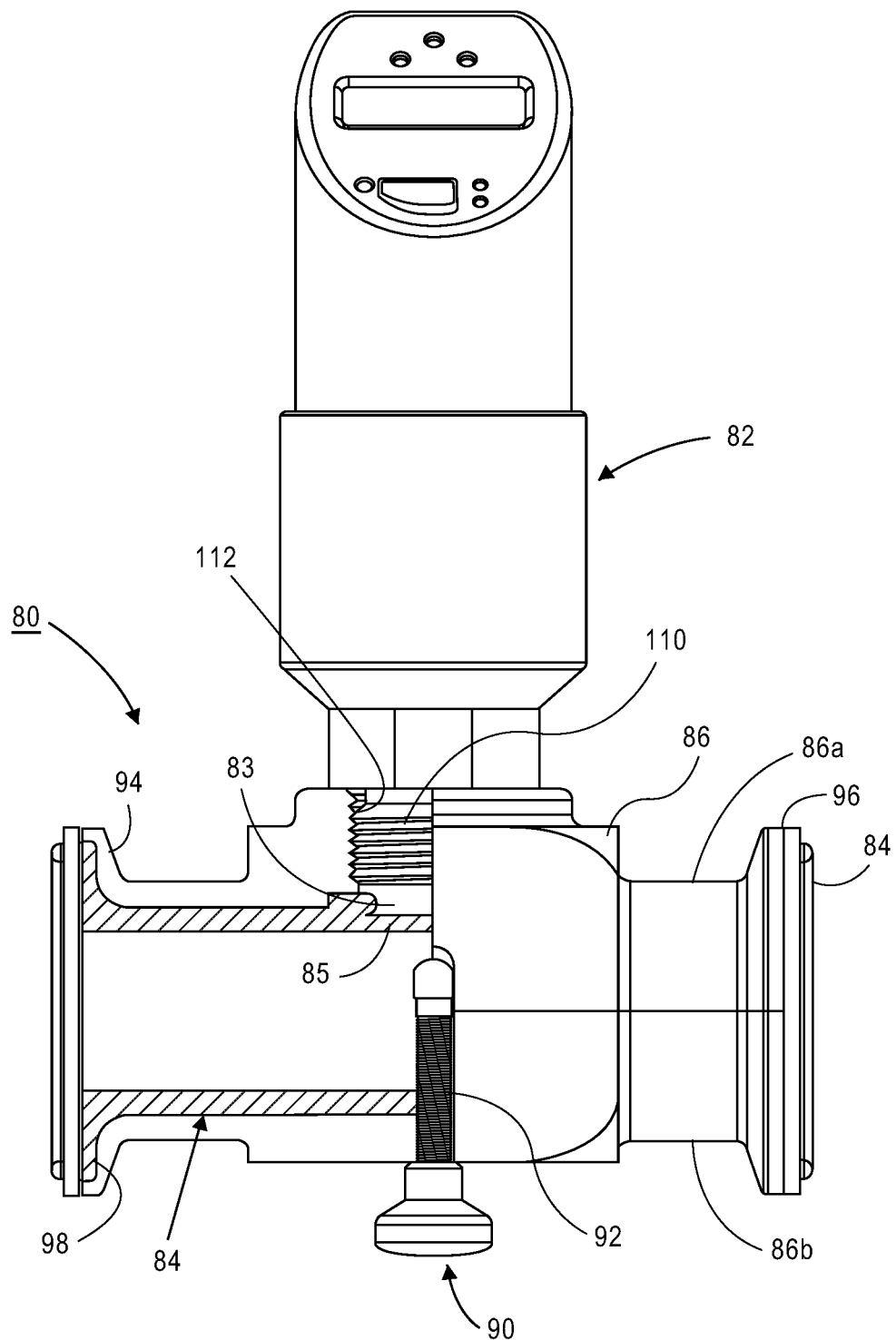
FIG. 4A illustrates a side view of a fluid monitoring assembly that includes a pressure sensor.
Figure 4B:
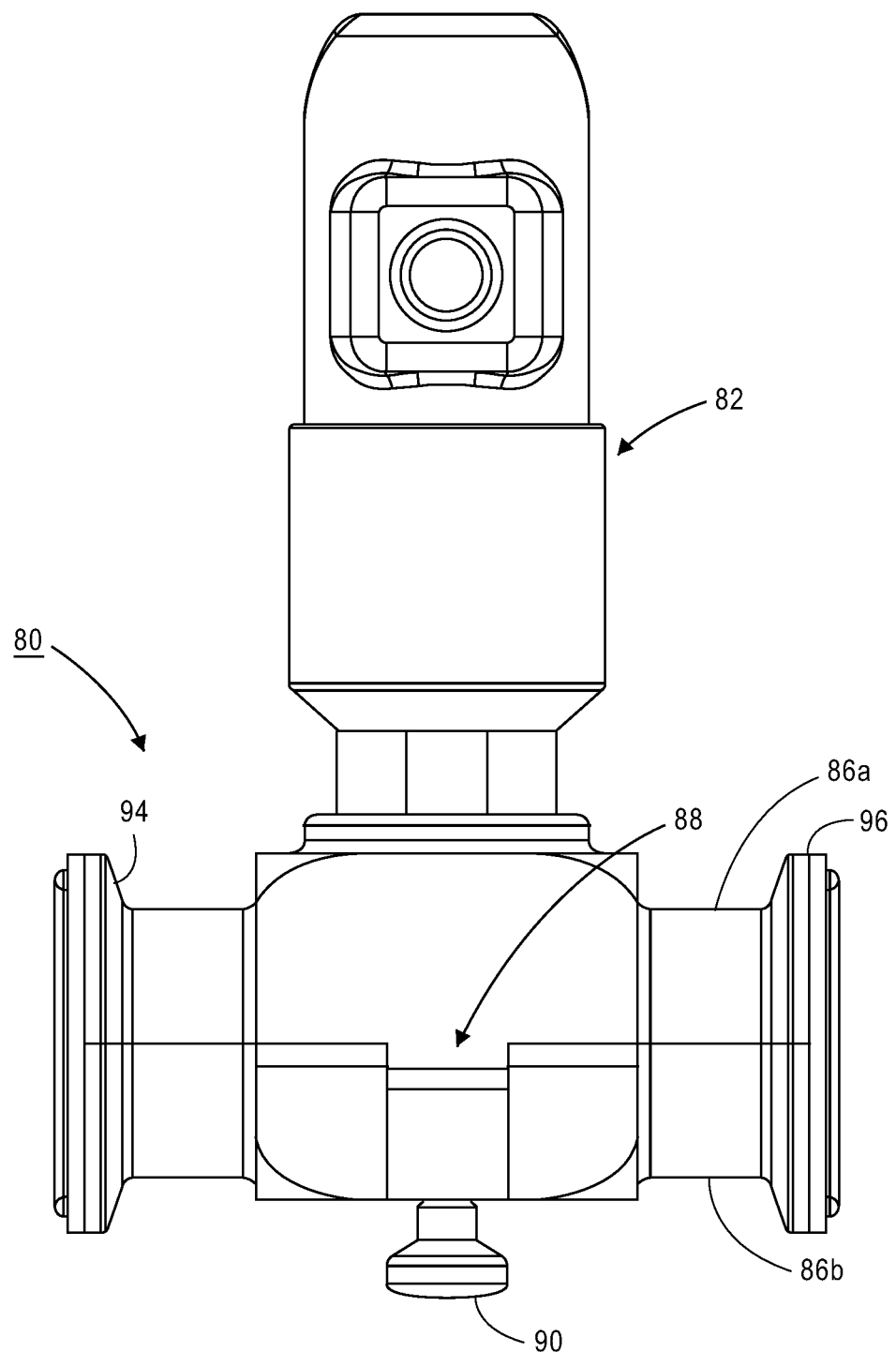
FIG. 4B illustrates an opposing side view of a fluid monitoring assembly that includes a pressure sensor.

FIGS. 4A-4E illustrate one embodiment of a fluid monitoring assembly 80 according to another embodiment. This embodiment pertains to a fluid monitoring assembly 80 that includes a pressure sensor 82 that has a pressure sensing end 83 that is in contact with a wall 85 of the silicone liner 84. The pressure sensor 82 and the silicone liner 84 are held in place with a two-part housing 86. In this embodiment, the silicone liner 84 can be made disposable while the housing 86 can be re-used with another new or un-used silicone liner 84. The pressure sensor 82 may also be reusable. The pressure sensor 82 may be made of any number of materials. In some alternative embodiments, a portion of the pressure sensor 82 may be from a UV curable material though this is not required. The housing 86 may be divided into two halves 86a, 86b that can be selectively opened and closed so that the silicone liner 84 may be replaced. The two halves 86a, 86b are moveable via the hinge 88 as seen in FIG. 4B. A fastener 90 such as a locking knob and associated locking arm 92 can be used to fixedly hold the two-part housing 86 in the closed state. As best seen in FIG. 4A, the two-part housing 86 includes flanges 94, 96 that are sized to contain the corresponding silicone flanges 98, 100 (best seen in FIG. 4C) of the silicone liner 44.

In an alternative embodiment, the flanges 98, 100 of the liner 44 may be omitted along with the flanges 94, 96 of the housing 86. The housing 86 may thus extend laterally beyond the location of the pressure sensor 82 and not terminate in a mating structure or flange-like surface. The housing 86 may continue on in any number of geometrical configurations. For example, the 86 housing may continue as a straight segment, a curved segment, elbow or the like.

Figure 4C:
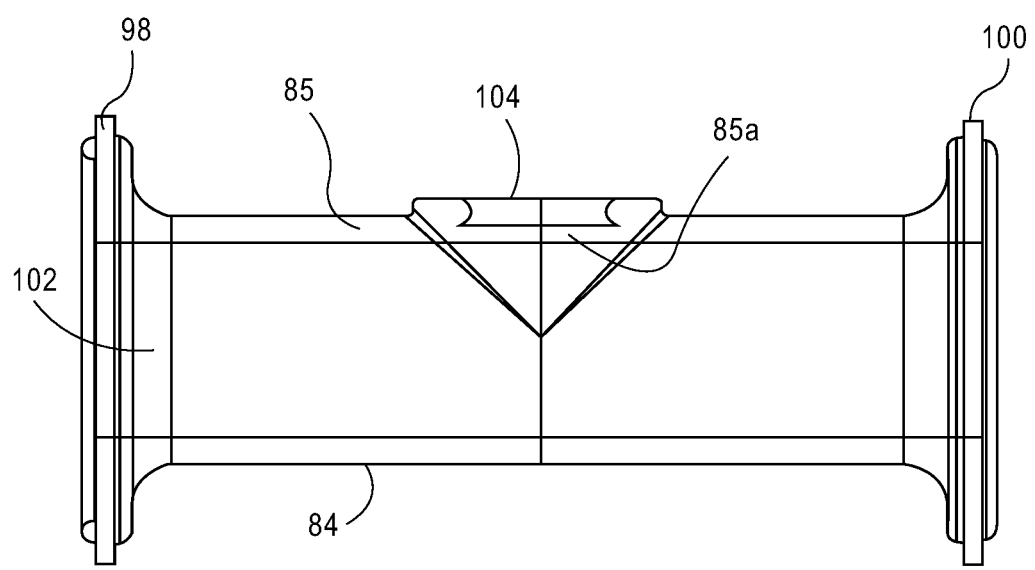
FIG. 4C illustrates a side view of a silicone liner used in the fluid monitoring assembly of FIG. 4A.

FIG. 4C illustrates the silicone liner 84. The silicone liner 84, like the prior embodiment, includes a wall 85 that defines a lumen 102 through which fluid passes (e.g., a segment of silicone tubing). The wall 85 includes a reduced thickness portion 85a seen in FIG. 4C which is interposed between the lumen 102 and the pressure sensing end 83 of the pressure sensor 82. During operation, pressure from the fluid within the lumen 102 is transferred via the reduced thickness portion 85a to the pressure sensing end 83. In this embodiment, the pressure of the fluid in the lumen 102 is measured indirectly via the wall 85 of the silicone liner 84—there is no direct contact of fluid against the pressure sensor 82. Fluid pressure within the lumen is transmitted through the wall 85 to the pressure sensing end 83 of the pressure sensor 82.

This is advantageous because there is no risk of contamination from contact with the pressure sensor 82. Further, the pressure sensor 82 may also be re-usable with another silicone liner 84. As seen in FIG. 4C, a recess 104 is formed in the wall 85 that receives the pressure sensing end 83 of the pressure sensor 82.

Figure 4D:
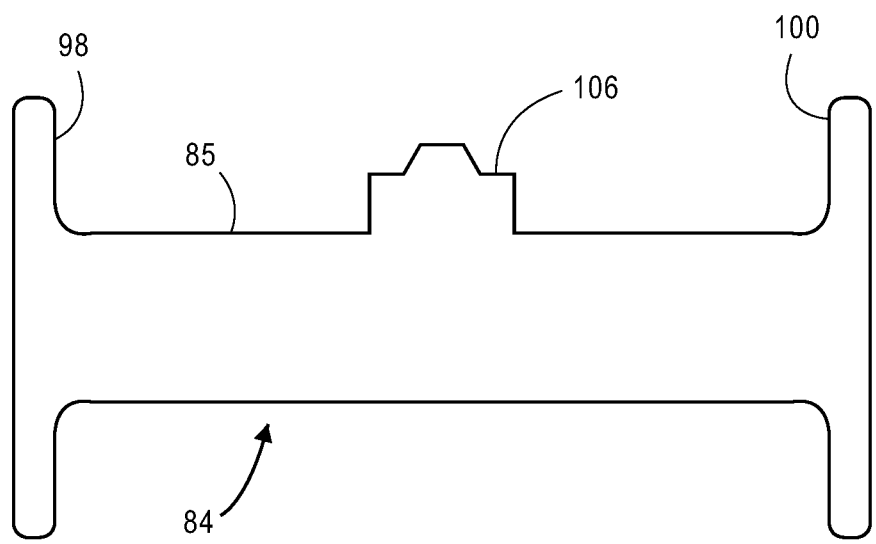
FIG. 4D illustrates one alternative of a silicone liner used in the fluid monitoring assembly of FIG. 4A.
Figure 4E:
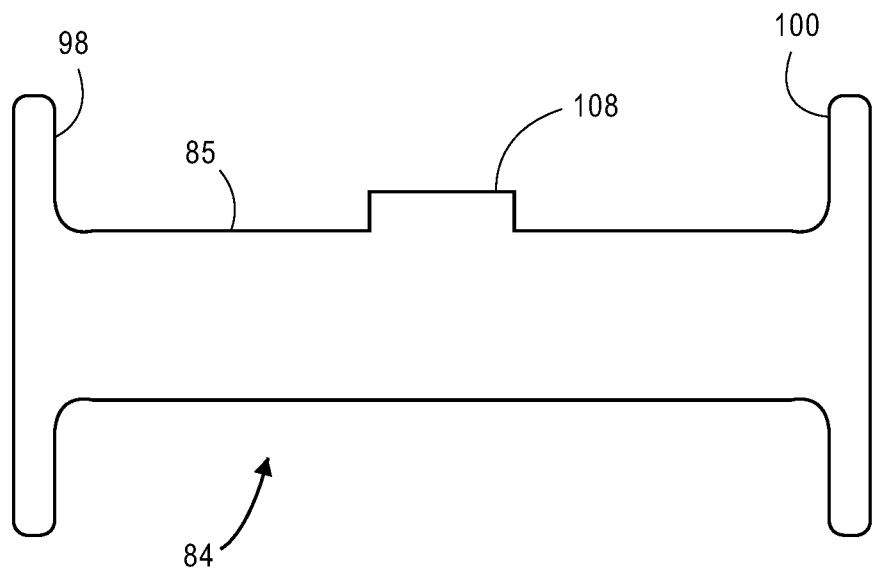
FIG. 4E illustrates another alternative of a silicone liner used in the fluid monitoring assembly of FIG. 4A.

The silicone liner 84 may be made using a heat-cured or UV cured process. In fact, in other embodiments, the liner 84 may be formed from a material other than silicone. Other configurations of the interface between the wall 85 of the silicone liner 84 and the pressure sensor 82 are contemplated. FIG. 4D illustrates a different embodiment wherein a nipple 106 projects from the wall 85 and interfaces with the pressure sensing end 83 of the pressure sensor 82. FIG. 4E illustrates an alternative embodiment wherein a button or region of increased thickness 108 in the wall 85 interfaces with the pressure sensing end 83 of the pressure sensor 85. The invention is not limited to the type of pressure sensor 82 that is used. Referring back to FIG. 4A, a commercially available Endress+Hauser pressure sensor 82 (Ceraphant T) is illustrated being used although it should be understood that other pressure sensors 82 may be used. The pressure sensor 82 may include any type of pressure sensor such as those that are diaphragm-based, strain-gauge based, semiconductor based, fluid-based, and the like. As seen in FIG. 4A, the pressure sensor 82 includes threads 110 that engage corresponding threads 112 in the two-part housing 86.

The two-part housing 86 is opened and closed as explained previously in the context of the embodiment of FIGS. 2A-2J. In particular, the fastener 90 is tightened or loosened to secure the two parts of the housing 86a, 86b together. The two-part housing 86 is preferably constructed of a metal such as stainless steel. However, in alternative embodiments, the two-part housing 46 may be made from plastic materials. Further, as noted above, other types of fasteners may be used. These include screws, nuts, clamps, bands, ties, and the like.

Figure 5D:
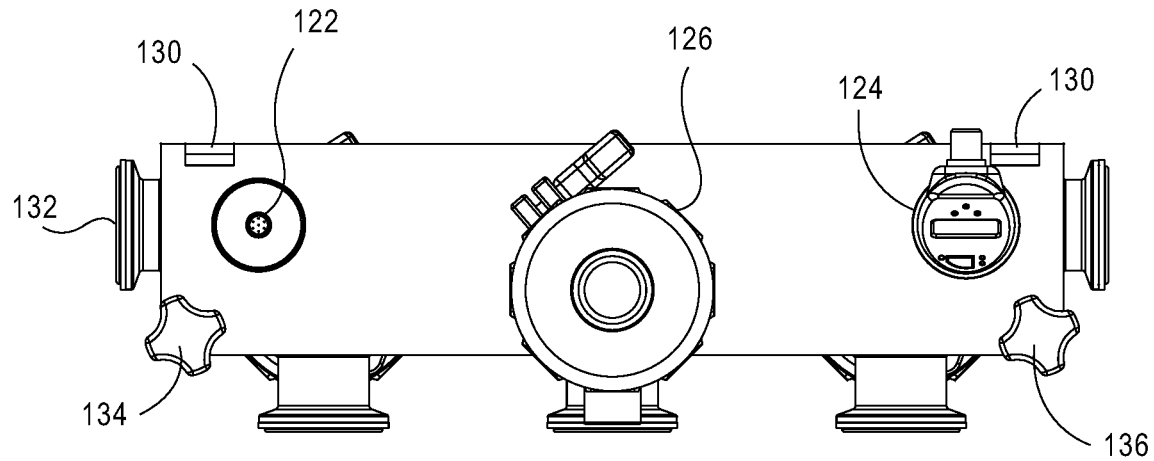
FIG. 5D illustrates a plan view of the fluid management assembly.

FIGS. 5A-5E and 6A-6D illustrate another embodiment of a fluid management assembly 120. This embodiment incorporates one or more sensors 122, 124 into an assembly that also contains one or more valves 126. With reference to FIGS. 5A-5E, the fluid management assembly 120 includes a housing 128 that is formed from a first portion 128a and a second portion 128b that may be brought or assembled together to form a single housing 128. In the embodiment of FIGS. 5A-5E, the first and second portions 128a, 128b are connected via a hinge 130. The housing 128 can thus be opened and closed so that an internal liner 132 can be selectively placed against facing surfaces of the first and second portions 128a, 128b. The facing surfaces of the first and second portions 128a, 128b contain corresponding hemispherical-shaped grooves that, when brought together as seen in FIG. 5A, encapsulate the liner 132. FIGS. 6A-6D illustrate one embodiment of the liner 132. The housing 128 may be formed from a metal (e.g., stainless steel) or polymer material (e.g., plastic material).

Figure 5E:
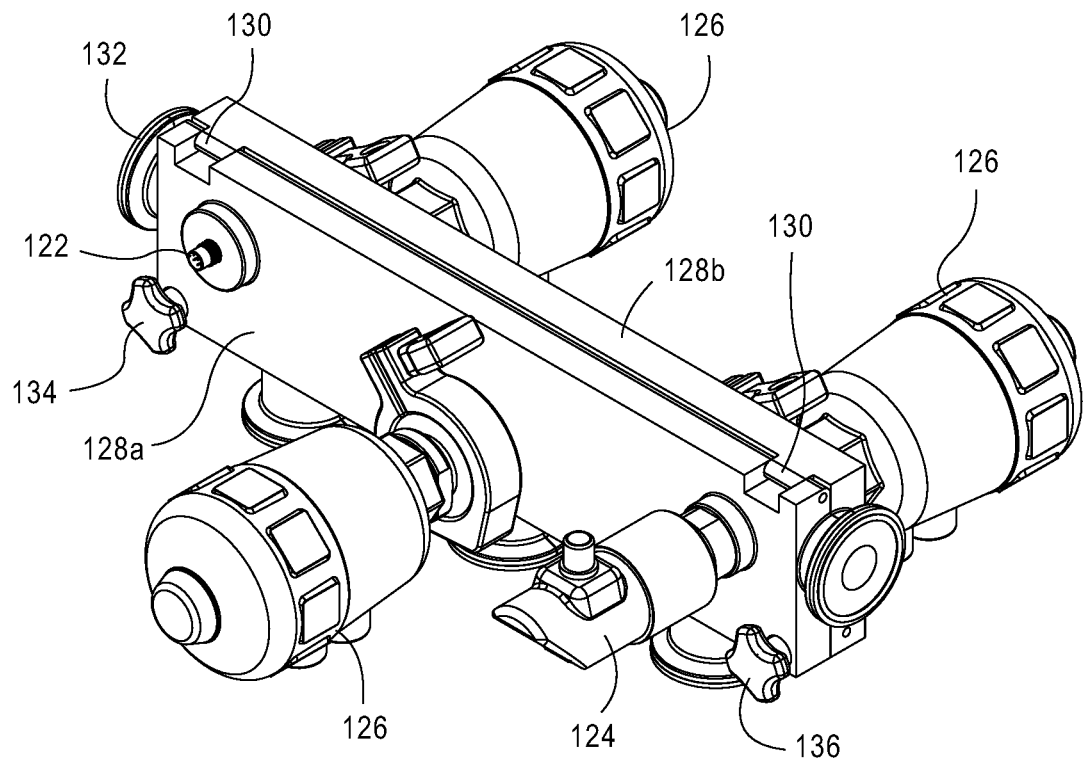
FIG. 5E illustrates a perspective view of a fluid management assembly.

The first and second portions 128a, 128b are held in a closed state via fasteners 134, 136. Fasteners 134, 136 may include a knob, screw, clamp, or the like. Two such fasteners 134, 136 are illustrated although a single fastener (or more fasteners) may be used in other embodiments. FIGS. 5A, 5D, and 5E illustrate three valves 126 that are secured to the housing 128 and are used to selectively pinch or otherwise close the liner 132 in a selective manner. The valves 126 may be manual valves or automatic valves (e.g., pneumatically activated or servo-type actuators). The valves 126 generally operate by having a stem or the like that can extend or retract as needed to prevent or enable fluid flow through the liner 132. These valves 126 can be located at a common conduit or branch pathway so that flow can be directed as desired. While three (3) such valves 126 are illustrated, more or less may be used.

In the embodiment of FIGS. 5A-5E, two different types of sensors 122, 124 are included in the assembly 120. The first sensor 122 includes a conductivity sensor 122 such as the type illustrated in FIGS. 2A-2J. In particular, the conductivity sensor 122 is at least partially embedded or potted within a wall of the liner 132. The conductivity sensor 122 illustrated in FIG. 5B includes electrodes 138 that are in conduct with product that passes through the lumen 140 of the liner 132. In some embodiments, the liner 132 may be formed from a UV-curable silicone. Alternatively, it may be possible to integrate the conductivity sensor 122 using a heat-curable silicone. In some embodiments, the liner 132 may be made of another polymer material besides silicone. FIG. 5C illustrates a second sensor 124 that is the form of a pressure sensor 124. The pressure sensing end 142 of the pressure sensor 124 is in contact with a portion of the wall of the liner 132, wherein fluid pressure within the lumen 140 is transmitted through the wall to the pressure sensing end 142. The portion of the wall of the liner 132 that is contact with the pressure sensing end 142 may include a reduced thickness portion like that shown in FIG. 5C or it may include a nipple or thickened region like the embodiments of FIGS. 4D and 4E.

FIGS. 6A-6D illustrate the liner 132 with the conductivity sensor 122 embedded therein. The contact region of the wall of the liner 132 that is in contact with the pressure sensing end 142 of the pressure sensor 124 can best be seen in FIG. 6C. In this embodiment, the liner 132 terminates at flanges 144a, 144b, 144c, 144d, and 144e. These flanges 144a, 144b, 144c, 144d, and 144e can then be used to connect to various other components/devices to the fluid management assembly 120. In some embodiments, the flanges 144a, 144b, 144c, 144d, and 144e are not encapsulated by corresponding flanges in the housing portions. In an alternative configuration, the housing 128 may integrate corresponding half flanges to contain the flanges 144a, 144b, 144c, 144d, and 144e. In still another alternative embodiment, neither the liner 132 nor the housing 128 may terminate in any flange-like structure. Rather, the housing 128 may extend laterally to cover extension of the liner 312. The housing 128, as explained herein, may take a number of different geometric configurations (e.g., elbows, bends, and straight segments).

Figure 7:
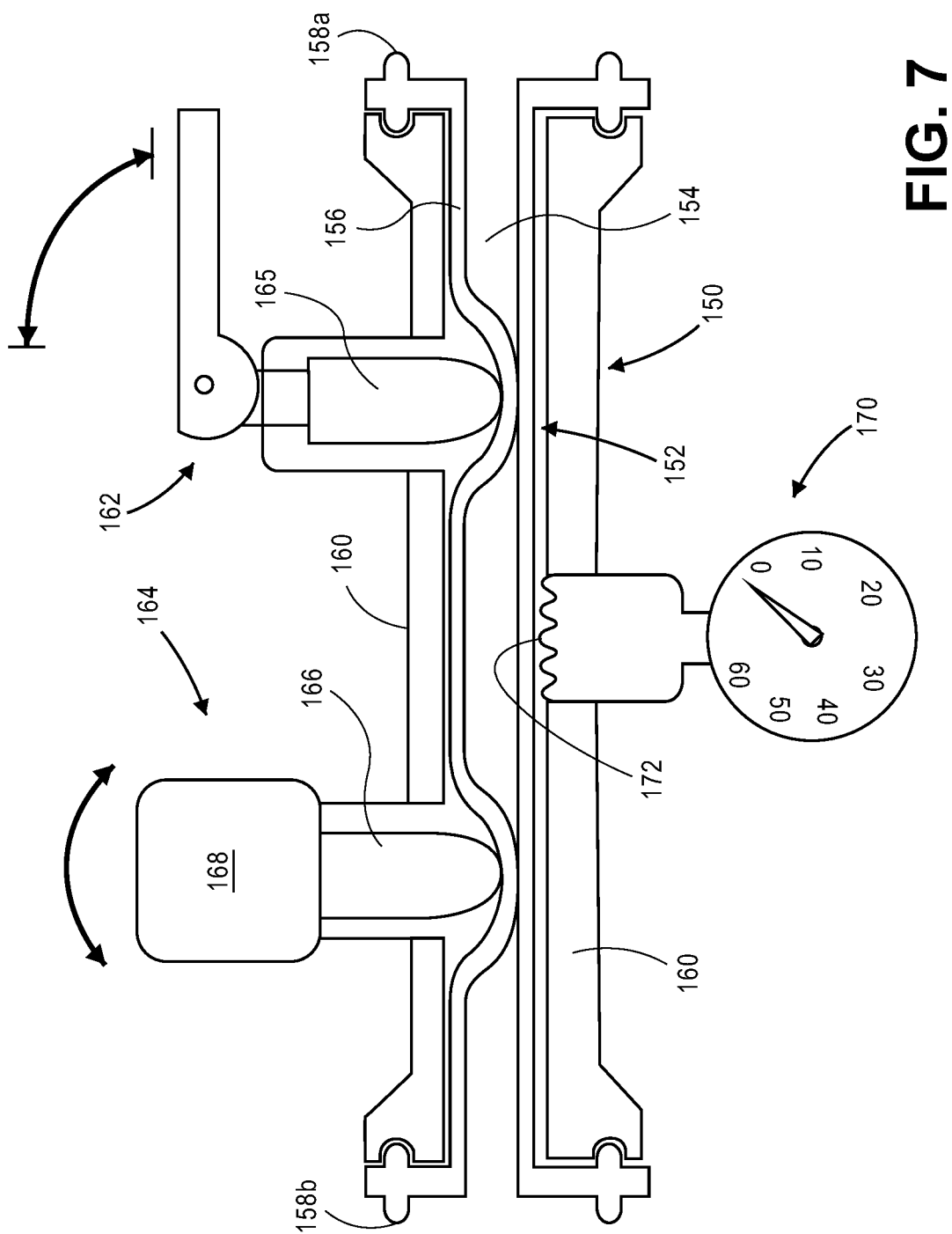
FIG. 7 illustrates another embodiment of a fluid management assembly.

FIG. 7 illustrates another embodiment of a fluid management assembly 150 according to one embodiment. In this embodiment, the fluid management assembly 150 contains one or more manually operated valves. The fluid management contains a liner 152 that is similar those previously discussed herein. The liner 152 is made from a polymer material such as silicone and includes a central lumen 154 that is defined by a wall structure 156. The liner 152 terminates at optional flanges 158a, 158b that can then be used to connect to other components/devices to the fluid management assembly 150. The fluid management assembly 150 includes a housing 160 that encapsulates the liner 152. FIG. 7 illustrates one half of the housing 160. It should be understood that the housing 160 may include a two component structure such as that illustrated in the embodiment of FIGS. 5A-5E where two halves of the housing 160 can be opened and closed via hinge(s) and closed using one or more fasteners (not shown). The housing 160 may be made from the polymeric or metallic material.

As seen in FIG. 7, the fluid management assembly 150 includes an on/off valve 162 in addition to a manually operated control valve 164. The on/off valve 162 is a toggle-type valve that has an "on" position and an "off" position. The on/off valve 162 operates by depressing (or not depressing) a plunger 165 within the fluid management assembly 150 to pinch or close flow within the liner 152. The manually operated control valve 164 also includes a plunger 166 that moves generally perpendicular to the axis of the liner 152 in response to a knob 168 that is turned. Turning of the knob 168 advances or retracts the plunger 166 so that the internal diameter of the liner 152 is adjusted to control the flow of fluid therein. As the plunger 166 compresses the liner 152 flow within the liner 152 is reduced. Conversely, as the plunger 166 is retracted, more fluid is able to flow within the liner 152.

Also illustrated in FIG. 7 is an optional pressure sensor 170 that is integrated into the fluid management assembly 150. The pressure sensor 170 extends through the housing 160 and places a pressure sending end 172 in contact with an outer surface of the liner 152. The pressure sensor 170 is able to detect and sense pressure of fluid within the liner 152 without direct contact with the fluid in one embodiment. As seen in FIG. 7, the pressure sensor 170 is an analog sensor though it should not be so limited. Any type of pressure sensor 170 including digital sensors may be used. In addition, at the location where the pressure sensing end 172 contacts the liner 152, the liner 152 may optionally include a thinned out or narrow wall portion.

In one alternative embodiment, a RF identification tag or chip (RFID) (not illustrated) may be embedded or otherwise located on or within one of the liners described herein. The RFID tag or chip may be used, for example, to track manufacturing information related to the liner (e.g., lot number, manufacturing date, manufacturing location, product type, etc.). The RFID tag or chip may also store information related when the liner or its associated sensor(s) have been installed or changed. The RFID tag or chip may also contain information pertaining to a sensor that is associated therewith. For example, some sensors may require a calibration curve or calibration parameters which can then be stored in the RFID tag or chip.

While embodiments of the present invention have been shown and described, various modifications may be made without departing from the scope of the present invention. For example, while the liners discussed herein have been described as being made of silicone other materials besides silicone may be used. As an alternative to UV-curable polymers, polymer materials that are curable at relatively low temperatures may be used. Other materials may also be envisioned that can work within the fluid monitoring assemblies described herein. For example, in some embodiments, the liners may be formed from a thermoplastic elastomer (TPE) or a thermoplastic rubber (TPR). For silicone, the liners may be unreinforced, reinforced, or braided silicon in some alternative embodiments. The invention, therefore, should not be limited, except to the following claims, and their equivalents.

What is claimed is:

1. A fluid monitoring assembly comprising:
   a segment of compressible unreinforced silicone tubing comprising a wall defining a lumen through which the fluid passes, the segment having a nipple that projects outwardly therefrom;
   a housing having first and second portions connected to one another at a hinge, the housing defining an interior portion configured to hold the segment of compressible unreinforced silicone tubing;
   a pressure sensor having a pressure sensing end in contact with an exterior portion of the nipple and configured to measure the pressure of fluid contained in the lumen of the compressible unreinforced silicone tubing, wherein the pressure sensor is secured in one of the first and second portions of the housing; and
   a fastener configured to hold the first and second portions in a closed state.

2. The fluid monitoring assembly of claim 1, wherein the housing comprises a metal.

3. The fluid monitoring assembly of claim 1, wherein the housing comprises a polymer.

4. The fluid monitoring assembly of claim 1, wherein the pressure sensing end is in contact with a portion of the nipple having a reduced thickness.

5. The fluid monitoring assembly of claim 1, wherein the pressure sensing end is in contact with a portion of the nipple having an increased thickness.

6. The fluid monitoring assembly of claim 1, further comprising at least one pinch valve mounted in the housing and configured to selectively pinch the segment of compressible unreinforced silicone tubing.

7. The fluid monitoring assembly of claim 1, the fastener comprises a knob and locking arm.

8. The fluid monitoring assembly of claim 1, wherein the segment of compressible unreinforced silicone tubing comprises a common segment and one or more branch segments.

9. The fluid monitoring assembly of claim 1, wherein the pressure sensor is removable from the housing.

10. The fluid monitoring assembly of claim 9, wherein the pressure sensor comprises threads that engage with corresponding threads in the housing.

11. The fluid monitoring assembly of claim 1, further comprising one or more additional non-pressure sensor sensors disposed on or in the housing.

12. The fluid monitoring assembly of claim 11, wherein the one or more additional sensors comprises at least one of a conductivity sensor, a temperature sensor, a turbidity sensor, and a pH sensor.

13. The fluid monitoring assembly of claim 1, further comprising a RF identification tag disposed on or within the compressible unreinforced silicone tubing.

14. The fluid monitoring assembly of claim 1, wherein the housing terminates in one or more flanges.

\* \* \* \* \*